(12) United States Patent
Duncan

(10) Patent No.: US 8,106,258 B2
(45) Date of Patent: Jan. 31, 2012

(54) USE OF A LOW-OXYGEN ENVIRONMENT IN PLANT TRANSFORMATION

(75) Inventor: David R. Duncan, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 17 days.

(21) Appl. No.: 10/905,204

(22) Filed: Dec. 21, 2004

(65) Prior Publication Data

US 2005/0138693 A1 Jun. 23, 2005

Related U.S. Application Data

(60) Provisional application No. 60/481,827, filed on Dec. 23, 2003.

(51) Int. Cl.
*A01H 1/00* (2006.01)
(52) U.S. Cl. .......................... 800/294; 800/295; 800/278
(58) Field of Classification Search .................. 800/294, 800/295, 278
See application file for complete search history.

(56) References Cited

U.S. PATENT DOCUMENTS

| 5,538,877 A * | 7/1996 | Lundquist et al. ............ 800/265 |
| 6,365,807 B1 * | 4/2002 | Christou et al. ........... 800/320.2 |
| 2002/0035739 A1 * | 3/2002 | Lassner et al. ................. 800/279 |

FOREIGN PATENT DOCUMENTS

| WO | WO 92/15675 | 9/1992 |
| WO | WO 92/20809 | 11/1992 |

OTHER PUBLICATIONS

Carman, J.G. "Improved somatic embryogenesis in wheat by partial simulation of the in-ovulo oxygen, growth-regulator and desiccation environments," Planta (1988) 175:417-424. (8 pages total).*
Shimada et al.; "Effects of Low O2 Concentration of Net Photosynthesis of C3 Plantlets In Vitro," Acta Horticulturae; 230; 1988; pp. 171-175. (5 pages total).*
Ishada et al.; "High efficiency transformation of maize (*Zea mays* L.) mediated by *Agrobacterium tumefaciens*," Nature Biotechnology, vol. 14, Jun. 1996; pp. 745-750. (6 pages total).*
Raineri, D.M. et al. "*Agrobacterium*-mediated Transformation of Rice," Biotechnology; vol. 8:33-38; Jan. 1990.*
Hansen et al. "Recent advances in the transformation of plants," Trends in Plant Science reviews, Jun. 1999, vol. 4, No. 6, pp. 226-231.*
Buddendorf-Joosten et al. "Components of the gaseous environment and their effects on plant growth and development in vitro," Plant Growth Regulations; 15:1-16; 1994.*
Chalandon et al. "*Agrobacterium* yellow group: bacterimia and possible septic arthritis following peripheral blood stem cell transplantation," Bone Marrow Transplantation (2000) 26, 101-104.*
Wise et al., "Culture and maintenance of *Agrobacterium* strains," Methods Molec. Bio., 343:3-13, 2006.*
Krieg et al. "Bergey's Manual of Systematic Bacteriology," vol. 1, 1984; p. 244 (3 pages total).*
Parrott et al. "*Agrobacterium* induces plant cell death in wheat (*Triticum aestivum* L.)," Physiological and Molecular Plant Pathology (2002) 60, 59-69.*
S. W. Adkins, Cereal Callus Cultures: Control of Headspace Gases can Optimise the Conditions for Callus Proliferation, *Aust. J. Bot.* 40:737-749 (1992).
Parrott et al., *Agrobacterium* induces plant cell death in wheat (*Triticum aestivaum* L.), Physiological and Molecular Plant Pathology 60:59-69 (2002).
European Patent Office Supplemental Search Report for PCT/US2004042970, Jan. 23, 2007.
Daneshvar et al., "CDC group O-3: phenotypic characteristics, fatty acid composition, isoprenoid quinone content, and in vitro antimicrobic susceptibilities of an unusual gram-negative bacterium isolated from clinical specimens," *J. of Clinical Microbiology*, 36(6):1674-1678, 1998.
Potvliege et al., "Catheter infection caused by an unusual pathogen, *Agrobacterium* radiobacter," *J. of Clinical Microbiology*, 27(9):2120-2122, 1989.
Swann et al., "*Agrobacterium* yellow group and pseudomonas paucimobilis causing peritonitis in patients receiving continuous ambulatory peritoneal dialysis," *J. Clin. Pathol.*, 38:1293-1299, 1985.
Takeuchi et al., "Taxonomic study of bacteria isolated from plants: proposal of *Sphingomonas rosa* sp. nov., *Sphingomonas prui* sp. nov., *Sphingomonas asaccharolytica* sp. nov., and *Sphingomonas mali* sp. nov.," *Int'l J. of Systematic Bacteriology*, 45(2):334-341, 1995.
Wise et al., "Culture and maintenance of *Agrobacterium* strains," *Methods Molec. Bio.*, 343:3-14, 2006.
Chong et al., "Anaerobic bacteria in routine diagnostic cultures," *Yonsei Medical J.*, 15(1):1-10, 1974.
Frost et al., "Relation to Environment," In: A Text-Book of General Bacteriology, The Macmillian Company, New York, (Eds. Frost et al.), pp. 131-133, 1911.
Genus *Agrobacterium* definition, Bergey's Manual of Determinative Bacteriology, Google Book Search, undated.
Jay et al., "Bioreactor studies on the effect of dissolved oxygen concentrations on growth and differentiation of carrot (*Daucus carota* L.) cell cultures," *Plant Cell Reports*, 11(12):605-608, 1992.
Rosenblatt et al., "Anaerobic bag culture method," *J. of Clinical Microbiology*, 1(6):527-530, 1975.
Sholevar et al., "Case 98—Bacteremia and a permanent intravascular catheter," path.upmc.edu, dated Mar. 1997.
Atwell et al., "The influence of oxygen deficiency on ethylene synthesis, 1-aminocyclopropane-1-carboxylic acid levels and aerenchyma formation in roots of zea mays," *Physiologia Plantarum*, 72:15-22, 1988.
Fransz et al., "An ultrastructural study on early callus development from immature embryos of the maize strains A188 and A632," *Acta Bot. Neerl.*, 36(3-4):247-260, 1987.
Gestel et al., Giant mitochondria are a response to low oxygen pressure in cells of tobacco (*Nicotiana tabacum* L.), *J. of Experimental Botany* 53: No. 371:1215-1218 (2002).

(Continued)

*Primary Examiner* — Susan McCormick Ewoldt

(74) *Attorney, Agent, or Firm* — SNR Denton US LLP; Thomas P. McBride

(57) ABSTRACT

Use of a low-oxygen environment before the transformation process can enhance transformation of plants. Low oxygen during regeneration can also increase the culturability of recalcitrant genotypes.

19 Claims, 1 Drawing Sheet

OTHER PUBLICATIONS

Hunt et al., Increased level of hemoglobin 1 enhances survival of hypoxic stress and promotes early growth in *Arabidopsis thaliana*, *PNAS* 99:No. 26:17197-17202 (2002).

Klok et al., Expression Profile Analysis fo the Low-Oxygen Response in Arabidopsis Root Cultures, *The Plant Cell* 14:2481-2494 (2002).

Mittler et al., Inhibition of Programmed Cell Death in Tobacco Plants during a Pathogen-Induced Hypersensitive Response at Low Oxygen Pressure, *The Plant Cell* 8:1991-2001 (1996).

Rolletschek et al., Legume embryos develop in a hypoxic environment, *J. of Experimental Botany* 53:No. 371: 1099-1107 (2002).

Sowa et al., Altering hemoglobin levels changes energy status in maize cells under hypoxia, *Proc. Natl. Acad. Sci. USA* 95:10317-10321 (1998).

Final Diagnosis—Agrobacterium radiobacter Bacteremia, Case 98, path.upmc.edu, dated Oct. 20, 2008.

Abedon, "Supplemental Lecture—Chapter: Bacteria Binomials," mansfield.ohio-state.edu, dated Apr. 26, 1998.

Adkins et al., "Cereal callus cultures: control of headspace gases can optimise the conditions for callus proliferation," *Aust. J. Bot.*, 40(6):737-749, 1992.

Adkins et al., "Rice callus physiology—identification of volatile emissions and their effects on culture growth," *Physiol.Plant.*, 78:526-531(1990).

Agrobacterium definition, A Dictionary of Horticultural Terms, floresflowers.com, dated Nov. 13, 2008.

Agrobacterium definition, University of Florida, grove.ufl.edu, dated Nov. 13, 2008.

Agrobacterium tumefaciens definition, King's Medical Library, kmle.com, dated Nov. 13, 2008.

Agrobacterium tumefaciens definition, Medicineword.com, dated Oct. 20, 2008.

Agrobacterium tumefaciens definition, Webster's Online Dictionary, websters-online-dictionary.org, dated Nov. 13, 2008.

Agrobacterium tumefaciens, Health Encyclopedia, steadyhealth.com, dated Nov. 13, 2000.

Aysan et al., "An outbreak of crown gall disease on rose caused by agrobacterium tumefaciens in Turkey," *Plant Pathology*, 52:780, 2003.

* cited by examiner

USE OF A LOW-OXYGEN ENVIRONMENT IN PLANT TRANSFORMATION

This application claims priority to U.S. Provisional Application 60/481,827, filed Dec. 23, 2003, herein incorporated by reference in its entirety.

BACKGROUND OF INVENTION

This invention relates to plant tissue culture conditions designed to more efficiently obtain transgenic plant cells, and more particularly to the use or incorporation of a low-oxygen environment in which to culture plant cells before transformation or during selection and regeneration.

The ability to transfer genes from a wide range of organisms to crop plants by recombinant DNA technology has become widespread in recent years. This advance has provided enormous opportunities to improve plant resistance to pests, disease, and herbicides, and to modify biosynthetic processes to change the quality of plant products. A highly efficient method for transformation of these crop plants continues to be a goal as there is a need for high capacity production of economically important plants.

Several technologies for the introduction of DNA into cells are well known to those of skill in the art and can be divided into categories including but not limited to: (1) chemical methods; (2) physical methods such as microinjection, electroporation, and particle bombardment; (3) viral vectors; (4) receptor-mediated mechanisms; and (5) *Agrobacterium*-mediated plant transformation methods.

*Agrobacterium*-mediated transformation is the most widely used method for transforming crop plants. Several *Agrobacterium* species mediate the transfer of a specific DNA known as "T-DNA", that can be genetically engineered to carry a desired piece of DNA into the selected plant species. The major events marking the process of T-DNA mediated pathogenesis and ultimate transformation are induction of virulence genes, processing and transfer of the T-DNA to the plant's genome.

Typically, *Agrobacterium*-mediated genetic transformation of plants involves several steps. The first step, in which the *Agrobacterium* and plant cells are first brought into contact with each other, is generally called "inoculation." Sometimes, the plant cells are "precultured" before inoculation. This is often to condition the cells to be more amenable to transformation. Following the inoculation step, the *Agrobacterium* and plant cells/tissues are usually grown together for a period of several hours to several days or more under conditions suitable for growth and T-DNA transfer. This step is termed "co-culture". Following co-culture and T-DNA delivery, the plant cells are often treated with bactericidal or bacteriostatic agents to prevent further growth of the *Agrobacterium*. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, one or more "selection" steps usually follow it. Both the "delay" and "selection" steps typically include bactericidal or bacteriostatic agents to prevent further growth of any remaining *Agrobacterium* cells because the growth of *Agrobacterium* cells is undesirable after the infection (inoculation and co-culture) process. Then the selected transgenic cells are put through a "regeneration" step in which transformed plantlets are produced.

Particle bombardment is another common method of transforming plants. In this method, particles are coated with nucleic acids and delivered into cells by a propelling force. Exemplary particles include those comprised of tungsten, platinum, or preferably, gold. An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with plant cells cultured in suspension. Microprojectile bombardment techniques are widely applicable and may be used to transform virtually any plant species. After bombardment of the plant tissues or cells, selection and regeneration are performed as described above for *Agrobacterium* transformation.

The present invention provides a novel improvement to the transformation process by providing a low-oxygen environment to the plants cells or tissue during at least one of the preculture, selection or regeneration phases of transformation. A continuing need exists in the field of plant transformation to produce a better quality of cell culture and to maximize genotypes with poor culture response or poor regeneration capabilities.

SUMMARY OF INVENTION

A method for genetically transforming a plant cell, tissue, or other suitable explant and regenerating a transformed plant therefrom is provided. In accordance with the present invention, the method provides for introducing a nucleic acid into the genome of a plant cell wherein the plant cell was previously cultured in a low-oxygen environment.

More specifically, the invention also provides a method for transforming dicotyledonous and monocotyledonous plant tissue and regenerating fertile transgenic plants therefrom comprising use of a low-oxygen environment before the transformation process.

The present invention further provides a method for selecting and regenerating a plant using a low-oxygen environment.

In another aspect, the present invention provides a transformed plant produced by exposing the plant tissue or cells to a low-oxygen environment during the transformation process.

DETAILED DESCRIPTION

Figure 1:
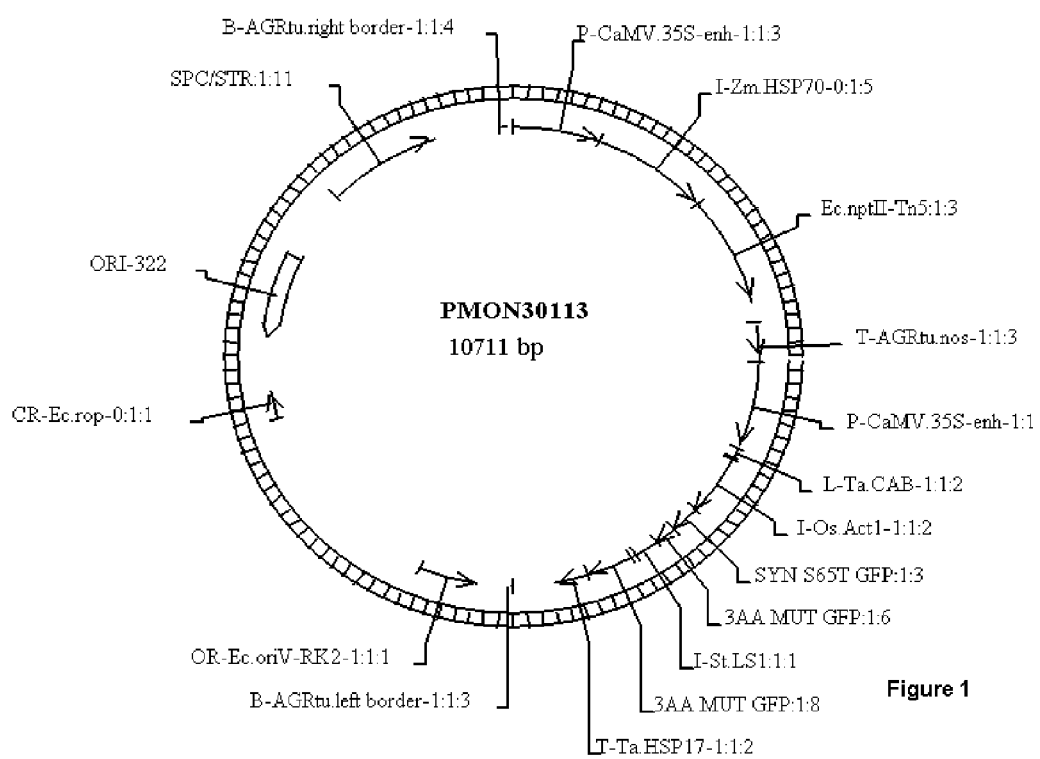
FIG. 1 is a schematic map of plasmid pMON30113.

It has been discovered that the culturing plant cells or tissue, more specifically, corn immature embryos or callus, in a low-oxygen environment prior to the transformation process increases the efficiency of transformation of the selected nucleic acid fragment. Also, use of the low-oxygen environment during the selection and regeneration process enhances the regenerability of plant tissues.

A "low-oxygen environment" is a tissue culture environment in which the oxygen level is below the ambient oxygen level of 21%. The oxygen level may be between about 2% and about 15% or between about 5% and about 9%. In one preferred embodiment, the oxygen level is about 7%. It is desirable to have a flow of gas in the low-oxygen environment to maintain a constant level of oxygen. A low-oxygen environment can be produced in several ways, which are known to one of skill in the art. A convenient method is to use an oxy-reducer made by BioSpherix (Redfield, N.Y.). The oxy-reducer is an oxygen probe that adjusts the oxygen level in a chamber by controlling the flow of nitrogen into the chamber.

The oxy-reducer is attached to a Percival chamber along with a supply of nitrogen gas. It controls the flow of nitrogen gas to maintain the set oxygen level in the chamber, which is not air-tight.

Other methods of producing a low-oxygen environment include, for example, using an air-tight chamber with a supply of low-oxygen compressed air that can be pumped through the chamber. In another example, a mixture of gases could be pumped into a chamber using an oxygen electrode to adjust the atmosphere in the chamber to the desired low-oxygen environment. The mixture could be adjusted by hand or by machine.

"Transformation media" or "plant transformation media" as used herein, refers to the plant tissue culture media, whether liquid, solid, or semi-solid, used during the process of the transformation of plant cells, tissues, parts, or other plant tissue explants and subsequent regeneration of whole, transgenic plants therefrom. Depending upon the plant species being transformed and the transformation process being used, the transformation media may include, but is not limited to, the isolation media, preculture media, induction media, inoculation media, delay media, selection media, or regeneration media.

"Efficiency of transformation or regeneration" or "transformation efficiency," as used herein, refers to the percentage of transgenic events produced per explant or the percentage of transgenic plants produced per explant. The efficiency of transformation may also be described in the number of "escapes" resulting from the transformation process.

"Plant cell or tissue" can include but is not limited to immature embryos, scutellar tissue, suspension cell cultures, immature inflorescence, shoot meristem, nodal explants, callus tissue, hypocotyl tissue, cotyledons, roots, and leaves.

An "event," as used herein, refers to a particular genomic insertion of the desired gene into a specific plant.

An "escape," as used herein, refers to a plant that survives the selection process without having the gene encoding for resistance to the selectable marker stably transformed into the plant genome.

In a preferred embodiment of the invention and as further detailed in the Examples below, a 7% oxygen environment during the pre-inoculation culture of immature embryos improves the efficiency of transformation. A 7% or 9% oxygen environment can also be used during selection and callus regeneration to further enhance the process. The two steps can be used separately or together in the same protocol.

As described herein, the use of a low-oxygen environment may advantageously be used with any plant species. Particularly preferred species for practice of the present invention include tomato, cotton, potato, wheat, corn, rice, and oilseeds, such as soybean, sunflower, and oilseed rape species.

The present invention provides for obtaining a fertile transgenic plant and a method for the transformation of plant cells or tissues and regeneration of the transformed cells or tissues into a fertile, differentiated transformed plant. Although various transformation systems are well known to those skilled in the art, a brief description of the process is provided below.

Typically, to initiate a transformation process in accordance with the present invention, it is first necessary to select the genetic components desired to be inserted into the plant cells or tissues. Genetic components may include any nucleic acid that is introduced into a plant cell or tissue using the method according to the invention. Genetic components can include non-plant DNA, plant DNA, or synthetic DNA.

In a preferred embodiment, the genetic components are incorporated into a DNA composition such as a recombinant, double-stranded plasmid or vector molecule comprising at least one or more of the following types of genetic components: (a) a promoter that functions in plant cells to cause the production of an RNA sequence, (b) a structural DNA sequence that causes the production of an RNA sequence that encodes a desired protein or polypeptide, and (c) a 3' non-translated DNA sequence that functions in plant cells to cause the polyadenylation of the 3' end of the RNA sequence. The vector may also contain a number of genetic components to facilitate transformation of the plant cell or tissue and regulate expression of the desired gene(s).

The genetic components are typically oriented so as to express an mRNA, which in one embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3' non-translated region that polyadenylates the 3' ends of the mRNA.

Means for preparing plasmids or vectors containing the desired genetic components are well known in the art. Vectors typically consist of a number of genetic components, including but not limited to regulatory elements such as promoters, leaders, introns, and terminator sequences. Regulatory elements are also referred to as cis- or trans-regulatory elements, depending on the proximity of the element to the sequences or gene(s) they control.

A region of DNA usually referred to as the "promoter" regulates transcription of DNA into mRNA. The promoter region contains a sequence of bases that signals RNA polymerase to associate with the DNA and to initiate the transcription into mRNA using one of the DNA strands as a template to make a corresponding complementary strand of RNA.

A number of promoters that are active in plant cells have been described in the literature. Such promoters include, but are not limited to, the nopaline synthase (NOS) and octopine synthase (OCS) promoters, which are carried on tumor-inducing plasmids of *Agrobacterium tumefaciens*; the caulimovirus promoters such as the cauliflower mosaic virus (CaMV) 19S and 35S promoters and the figwort mosaic virus (FMV) 35S promoter; the enhanced CaMV35S promoter (e35S); and the light-inducible promoter from the small subunit of ribulose bisphosphate carboxylase (ssRUBISCO, a very abundant plant polypeptide). All of these promoters have been used to create various types of DNA constructs that have been expressed in plants. Promoter hybrids can also be constructed to enhance transcriptional activity or to combine desired transcriptional activity, inducibility, and tissue or developmental specificity.

Thus, promoters that function in plants may be inducible, viral, synthetic, constitutive as described, temporally regulated, spatially regulated, and/or spatio-temporally regulated. Other promoters that are tissue-enhanced, tissue-specific, or developmentally regulated are also known in the art and envisioned to have utility in the practice of this invention. Useful promoters may be obtained from a variety of sources such as plants and plant DNA viruses. As described below, it is preferred that the particular promoter selected should be capable of causing sufficient expression to result in the production of an effective amount of the gene product of interest.

The promoters used in the DNA constructs (i.e., chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain one or more "enhancer sequences" to assist in elevating gene expression.

The mRNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes. Other genetic components that serve to enhance expression or affect transcription or translation of a gene are also envisioned as genetic components. The 3' non-translated region of the chimeric constructs preferably contains a transcriptional terminator, or an element having equivalent function, and a polyadenylation signal, which functions in plants to cause polyadenylation of the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (European Patent Application 385,962, herein incorporated by reference in its entirety).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

In many transformation systems, it is necessary for the transformation vector to contain a selectable, screenable, or scorable marker gene. These genetic components are also referred to herein as functional genetic components, as they produce a product that serves a function in the identification of a transformed plant, or a product of desired utility. The DNA that serves as a selection device functions in a regenerable plant tissue to produce a compound that confers upon the plant tissue resistance to an otherwise toxic compound. Genes of interest for use as a selectable, screenable, or scorable marker would include, but are not limited to, β-glucuronidase (GUS), green fluorescent protein (GFP), luciferase (LUX), antibiotics like kanamycin (Dekeyser et al., Plant Physiol., 90:217-223, 1989), and herbicides like glyphosate (Della-Cioppa et al., Bio/Technology, 5:579-584, 1987). Other selection devices can also be implemented, including, but not limited to, tolerance to phosphinothricin, bialaphos, and positive selection mechanisms Joersbo et al., Mol. Breed., 4:111-117, 1998) and would still fall within the scope of the present invention.

The present invention can be used with any suitable plant transformation plasmid or vector containing a selectable or screenable marker and associated regulatory elements as described, along with one or more nucleic acids (a structural gene of interest) expressed in a manner sufficient to confer a particular desirable trait. Examples of suitable structural genes of interest envisioned by the present invention would include, but are not limited to, genes for insect or pest tolerance, genes for herbicide tolerance, genes for quality improvements such as yield, nutritional enhancements, environmental or stress tolerances, or genes for any desirable changes in plant physiology, growth, development, morphology, or plant product(s).

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech Gen. Engin. Rev., 9:207-227, 1991). The RNA could also be a catalytic RNA molecule (i.e., a ribozyme) engineered to cleave a desired endogenous mRNA product (see for example, Gibson and Shillitoe, Mol. Biotech. 7:125-137, 1997). More particularly, for a description of anti-sense regulation of gene expression in plant cells see U.S. Pat. No. 5,107,065 and for a description of gene suppression in plants by transcription of a dsRNA see U.S. Pat. No. 6,506,559, U.S. Patent Application Publication No. 2002/0168707 A1, and U.S. patent applications Ser. No. 09/423,143 (see WO 98/53083), Ser. No. 09/127,735 (see WO 99/53050) and Ser. No. 09/084,942 (see WO 99/61631), all of which are incorporated in their entirety herein by reference. Thus, any gene that produces a protein or mRNA that expresses a phenotype or morphology change of interest is useful for the practice of the present invention.

Exemplary nucleic acids that may be introduced by the methods encompassed by the present invention include, for example, DNA sequences or genes from another species, or even genes or sequences that originate with or are present in the same species but are incorporated into recipient cells by genetic engineering methods rather than classical reproduction or breeding techniques. The term exogenous, however, is also intended to refer to genes that are not normally present in the cell being transformed or to genes that are not present in the form, structure, etc., as found in the transforming DNA segment or to genes that are normally present but a different expression is desirable. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In light of this disclosure, numerous other possible selectable or screenable marker genes, regulatory elements, and other sequences of interest will be apparent to those of skill in the art. Therefore, the foregoing discussion is intended to be exemplary rather than exhaustive.

Several technologies for the introduction of DNA into cells are well known to those of skill in the art and can be divided into categories including but not limited to: (1) chemical methods; (2) physical methods such as microinjection, electroporation and particle bombardment; (3) viral vectors; (4) receptor-mediated mechanisms; and (5) *Agrobacterium*-mediated plant transformation methods.

Most commonly, after the construction of the plant transformation vector or construct, the nucleic acid molecule, prepared as a DNA composition in vitro, is introduced into a suitable host such as *E. coli* and mated into another suitable host such as *Agrobacterium*, or directly transformed into competent *Agrobacterium*. These techniques are well-known to those of skill in the art and have been described for a number of plant systems including soybean, cotton, and wheat. Those of skill in the art would recognize the utility of *Agrobacterium*-mediated transformation methods. Preferred strains include, but are not limited to, *Agrobacterium tumefaciens* strain C58, a nopaline strain that is used to mediate the transfer of DNA into a plant cell; octopine strains, such as LBA4404; or agropine strains, e.g., EHA101, EHA105, or EHA109. The use of these strains for plant transformation has been reported, and the methods are familiar to those of skill in the art.

The present invention can be used with any transformable cell or tissue. Those of skill in the art recognize that transformable plant tissue generally refers to tissue that can have exogenous DNA inserted in its genome and under appropriate culture conditions can form into a differentiated plant. Such tissue can include, but is not limited to, callus tissue, hypocotyl tissue, cotyledons, meristematic tissue, roots, and leaves. For example, transformable tissues can include calli or embryoids from anthers, microspores, inflorescences, and leaf tissues. Other tissues are also envisioned to have utility in the practice of the present invention, and the desirability of a particular explant for a particular plant species is either known in the art or may be determined by routine screening and testing experiments whereby various explants are used in the transformation process and those that are more successful in producing transgenic plants are identified. The present invention is mostly likely to be useful with explants removed from environments that are naturally low in oxygen. In one embodiment of the present invention, immature corn embryos are used as the starting explant material.

Methods for transforming dicots by use of *Agrobacterium tumefaciens*, and obtaining transgenic plants have been published for a number of crops including cotton, soybean, *Brassica*, and peanut.

Successful transformation of monocotyledonous plants by *Agrobacterium*-based methods have also been reported. Transformation and plant regeneration have been achieved and reported at least in asparagus, barley, maize, oat, rice, sugarcane, tall fescue, and wheat.

The present invention finds particular use in *Agrobacterium*-mediated transformation processes. Positive results have also been obtained with biolistic transformation. Immature corn embryos are removed and precultured for 7 to 14 days in a low-oxygen environment. The precultured embryos then can be transformed via biolistics or inoculated with *Agrobacterium*. *Agrobacterium*-inoculated explants are typically cultured on an appropriate co-culture medium to allow for transfer of the genetic component containing the gene of interest to be introduced into the plant cells/tissue for incorporation into its genome. Appropriate co-culture media are typically known for each culture system or can be determined by one of skill in the art.

The *Agrobacterium*-inoculated explants are then typically cultured on an appropriate medium containing an agent to inhibit *Agrobacterium* growth. This medium is usually referred to as a delay medium or a selection medium, as described below. The *Agrobacterium*-inoculated explants are cultured on such a medium generally from about one to about fourteen days, preferably from about two to about seven days. Those of skill in the art are aware of the appropriate media components to inhibit *Agrobacterium* growth. Such media components include, but are not limited to, antibiotics such as carbenicillin or cefotaxime. After the culture step to inhibit *Agrobacterium* growth, and preferably before the explants can be placed on selective media, they can be analyzed for efficiency of DNA delivery by a transient assay that detects the presence of a gene contained on the transformation vector, including, but not limited to, a screenable marker gene such as the gene that codes for β-glucuronidase (GUS). The total number of blue spots (indicating GUS expression) for a selected number of explants is used as a positive correlation of DNA transfer efficiency.

In a preferred embodiment, after incubation on non-selective medium containing the antibiotics to inhibit *Agrobacterium* growth without selective agents (delay medium), the explants are cultured on selective growth medium including, but not limited to, a callus-inducing medium containing a selective agent. Typical selective agents have been described and include, but are not limited to, antibiotics such as geneticin (G418), paromomycin, kanamycin, or other chemicals such as glyphosate. Selection may be carried out in a low-oxygen environment. The plant tissue cultures surviving the selection medium are subsequently transferred to a regeneration medium suitable for the production of transformed plantlets. Regeneration can be carried out over several steps. The regeneration may also be conducted in a low-oxygen environment. Those of skill in the art are aware of the numerous types of media and transfer requirements that can be implemented and optimized for each plant system for plant transformation and regeneration. Consequently, such media and culture conditions disclosed in the present invention can be modified or substituted with nutritionally equivalent components, or similar processes for selection and regeneration, and still fall within the scope of the present invention.

The transformants produced are subsequently analyzed to determine the presence or absence of a particular nucleic acid of interest contained on the transformation vector. Molecular analyses can include, but are not limited to, Southern blots (Southern, Mol. Biol., 98:503-517, 1975) or PCR (polymerase chain reaction) analyses. These and other well known methods can be performed to confirm the stability of the transformed plants produced by the methods disclosed. These methods are well known to those of skill in the art and have been reported (see, for example, Sambrook et al., *Molecular Cloning: A Laboratory Manual*, Second Edition, Cold Spring Harbor Laboratory Press, Cold Spring Harbor, N.Y., 1989).

The previous discussion is merely a broad outline of standard transformation and regeneration protocols. One of skill in the art knows that specific crops and specific protocols can vary somewhat from the broad outline. A variety of media can be used in each system as well. Those of skill in the art are familiar with the variety of tissue culture media that, when supplemented appropriately, support plant tissue growth and development. These tissue culture media can either be purchased as a commercial preparation or custom prepared and modified by those of skill in the art. Examples of such media include, but are not limited to, Murashige and Skoog (Murashige and Skoog, Physiol. Plant, 15:473-497, 1962), N6 (Chu et al., Scientia Sinica 18:659, 1975), Linsmaier and Skoog (Linsmaier and Skoog, Physio. Plant., 18: 100, 1965), Uchimiya and Murashige (Uchimiya and Murashige, Plant Physiol. 15:473, 1962), Gamborg"s media (Gamborg et al., Exp. Cell Res., 50:151, 1968), D medium (Duncan et al., Planta, 165:322-332, 1985), McCown"s Woody plant media (McCown and Lloyd, HortScience 16:453, 1981), Nitsch and Nitsch (Nitsch and Nitsch, Science 163:85-87, 1969), and Schenk and Hildebrandt (Schenk and Hildebrandt, Can. J. Bot. 50:199-204, 1972) or derivations of these media supplemented accordingly. Those of skill in the art are aware that media and media supplements such as nutrients and growth regulators for use in transformation and regeneration are usually optimized for the particular target crop or variety of interest.

EXAMPLES

The following examples further illustrate the present invention. They are in no way to be construed as a limitation in scope and meaning of the claims.

Example 1

Bacterial Strains and Plasmids

*Agrobacterium tumefaciens* strain ABI is harbored with the binary vector pMON30113 (FIG. 1). The T-DNA in pMON30113 contains a neomycin phosphotransferase II gene (nptII) as the selectable marker and a green fluorescence protein gene (gfp) screenable marker, both driven by an e35S promoter.

Example 2

Preparation of *Agrobacterium*

*Agrobacterium* ABI containing a vector in glycerol stock is streaked out on solid LB medium supplemented with antibiotics kanamycin (50 mg/L), spectinomycin (100 mg/L), streptomycin (100 mg/L) and chloramphenicol (25 mg/L) and incubated at 28° C. for 3 days. Two days before *Agrobacterium* inoculation of the maize immature embryos, one colony or a small loop of *Agrobacterium* from the *Agrobacterium* plate is picked up and inoculated into 50 mL of liquid LB medium supplemented with 50 mg/L of spectinomycin, 50 mg/L streptomycin, 25 mg/L chloramphenicol, and 50 mg/L of kanamycin in a 250-mL flask. The flask is placed on a shaker at approximately 200 rpm and 28° C. overnight. One day before inoculation, the *Agrobacterium* cells are spun down at 3500 rpm for 15 min. The bacterium cell pellet is re-suspended in induction broth with 200 µM of acetosyringone and 50 mg/L spectinomycin, 50 mg/L streptomycin, 25 mg/L chloramphenicol, and 25 mg/L kanamycin and the cell density was adjusted to 0.25 at $O.D._{660}$. The bacterium cell culture (50 mL in each 250-mL flask) is then put back on the shaker and grown overnight. On the morning of inoculation day, the bacterium cells are spun down and washed with liquid ½MSVIC medium (2.2 g/L GIBCO (Carlsbad, Calif.) MS salts, 2 mg/L glycine, 0.5 g/L niacin, 0.5 g/L L-pyridoxine-HCl, 0.1 mg/L thiamine, 115 g/L L-proline, 10 g/L D-glucose, and 10 g/L sucrose, pH 5.4) supplemented with 200 µM of acetosyringone. After one more spinning, the bacterium cell pellet is re-suspended in ½MSVIC medium with 200 µM of acetosyringone, and the cell density is adjusted to 0.25 at $O.D._{660}$ for inoculation. One of skill in the art may substitute other media for ½MSVIC.

Reagents are commercially available and can be purchased from a number of suppliers (see, for example Sigma Chemical Co., St. Louis, Mo.).

Example 3

Explant Preparation and Preculture

Several genotypes of corn are used in this study. Ears containing immature embryos are harvested approximately 10 days after pollination and kept refrigerated at 4° C. until use (up to 5 days post-harvest). The preferred embryo size for this method of transformation is ~1.0-2.0 mm. This size is usually achieved 10 days after pollination inside the green house with the growth conditions of an average temperature of 30° C., day length of 14 hours with supplemental lighting supplied by GE 1000 Watt High Pressure Sodium lamps.

Isolated immature embryos are put embryonic axis side down on 211 medium (N6 salts, 2% sucrose, 1 mg/L 2,4-D, 0.5 mg/L niacin, 1.0 mg/L thiamine-HCl, 0.91 g/L L-asparagine, 100 mg/L myo-inositol, 0.5 g/L MES, 100 mg/L casein hydrolysate, 1.6 g/L $MgCl_2$, 0.69 g/L L-proline, 2 g/L GELGRO™, pH 5.8) containing 16.9 mg/L $AgNO_3$ (designated medium 211V), and incubated at 27° C. for 8 to 13 days. Embryos are incubated in either ambient air (21% oxygen) or in a low-oxygen environment (7% oxygen). In the low-oxygen environment, the callus formed is of higher quality than that in the ambient air.

Example 4

Inoculation and Co-Culture

After 8 to 13 days of preculture, the calli are transferred into an empty Petri plate and submerged by the prepared *Agrobacterium* cell suspension. After 30 minutes, the *Agrobacterium* cell suspension is removed using a fine-tipped sterile transfer pipette, and the calli are washed for 1 to 5 minutes in ⅟₁₀MSVIC medium with 200 µM acetosyringone and 20 µM silver nitrate. After the final aspiration, calli are transferred to fresh plates with sterile Whatman #5 filter paper. Plates are wrapped in parafilm and are cultured in a dark incubator (23° C.) for approximately 3 days.

The transformation efficiency in 7% oxygen increased from 2-fold to 6-fold from ambient air (Table 1). Transformation efficiency was increased the most in genotypes that are recalcitrant to callus formation and that are difficult to culture.

TABLE 1

Transformation efficiency of immature embryos with preculture in 7% or 21% oxygen.

| Experiment | 21% oxygen | 7% oxygen |
| --- | --- | --- |
| 1 | 2.4% | 4.8% |
| 2 | 5.4% | 9.6% |
| 3 | 3.2% | 15.5% |
| 4 | 2.6% | 16.7% |
| 5 | 2.6% | 12.4% |
| Avg. | 3.24 | 11.8 |

Example 5

Selection, Regeneration and Growth of Transformants with Paromomycin Selection

After 3 days, calli were transferred onto 211 medium supplemented with 200 mg/L paromomycin, 100 µM silver nitrate, and 500 mg/L carbenicillin to inhibit *Agrobacterium* in Petri dishes (100 mm×25 mm). The cultures were incubated in a dark culture room at 27° C. for 2-3 weeks. Calli were then transferred to 211 medium supplemented with 200 mg/L paromomycin and cultured in the dark for 3 weeks at 27° C. Resistant callus pieces were then transferred individually onto the first regeneration medium (217A, N6 salts, 1 mg/L thiamine-HCl, 0.5 mg/L niacin, 3.52 mg/L benzylaminopurine, 0.91 mg/L L-asparagine monohydrate, 100 mg/L myo-inositol, 0.5 g/L MES, 1.6 g/L $MgCl_2$-$6H_2O$, 100 mg/L casein hydrolysate, 0.69 g/L L-proline, 20 g/L sucrose, 2 g/L GELGRO™, pH 5.8) and incubated in the dark for 5 to 7 days. They were then transferred onto the second regeneration medium (MS salts, MS vitamins, 60 g/L sucrose, 6 g/L Phytagar, pH 5.8) in a petri dish (100 mm×25 mm) for approximately 4 to 6 weeks. All the callus pieces with regenerating shoots and living tissue were transferred onto the same medium contained in phytatrays for shoots to grow further before being moved to soil. The regeneration media were all supplemented with 250 mg/L carbenicillin and 200 mg/L paromomycin.

Regeneration can be done in a low-oxygen environment. In one experiment, regeneration in 7% oxygen increased the regeneration rate from 30% to 39%. In another experiment, the regeneration rate was increased from 21% to 49% in a 9% oxygen atmosphere.

Example 6

Methods of Microprojectile Bombardment

Approximately four hours prior to microprojectile bombardment, immature embryos were transferred to medium 211SV (medium 211V with the addition of sucrose to 12%). Twenty-five immature embryos were placed in a 60×15 mm petri dish, arranged in a 5×5 grid with the coleoptilar end of the scutellum pressed slightly into the culture medium at a 20 degree angle. Tissue was maintained in the dark prior to bombardment.

Prior to microprojectile bombardment, a suspension of gold particles was prepared onto which the desired DNA was precipitated. Ten milligrams of 0.6 μm gold particles (Bio-Rad) were suspended in 50 μL buffer (150 mM NaCl, 10 mM Tris-HCl, pH 8.0). Twenty-five μL of a 2.4 nM solution of the desired DNA was added to the suspension of gold particles and gently vortexed for about five seconds. Seventy-five μL of 0.1M spermidine was added and the solution vortexed gently for about 5 seconds. Seventy-five μL of a 25% solution of polyethylene glycol (3000-4000 molecular weight, American Type Culture Collection) was added and the solution was gently vortexed for five seconds. Seventy-five μL of 2.5 M $CaCl_2$ was added and the solution vortexed for five seconds. Following the addition of $CaCl_2$, the solution was incubated at room temperature for 10 to 15 minutes. The suspension was subsequently centrifuged for 20 seconds at 12,000 rpm (Sorval MC-12V centrifuge) and the supernatant discarded. The gold particle/DNA pellet was washed twice with 100% ethanol and resuspended in 10 mL 100% ethanol. The gold particle/DNA preparation was stored at −20° C. for up to two weeks.

DNA was introduced into maize cells using the electric discharge particle acceleration gene delivery device (U.S. Pat. No. 5,015,580). The gold particle/DNA suspension was coated on Mylar sheets (Du Pont Mylar polyester film type SMMC2, aluminum coated on one side, over-coated with PVDC co-polymer on both sides, cut to 18 mm square) by dispersion of 310 to 320 μL of the gold particle/DNA suspension on a sheet. After the gold particle suspension settled for one to three minutes, excess ethanol was removed and the sheets were air dried. Microprojectile bombardment of maize tissue was conducted as described in U.S. Pat. No. 5,015,580. AC voltage may be varied in the electric discharge particle delivery device. For microprojectile bombardment of precultured immature embryos, 35% to 45% of maximum voltage was preferably used. Following microprojectile bombardment, tissue was cultured in the dark at 27° C. Tissue is then selected and regenerated as described in Example 4.

In an experiment, preculturing immature embryos in 7% oxygen led to an increase in transformation efficiency from 0.25% to 3%.

All publications, patents, and patent applications mentioned in this specification are indicative of the level of skill of those skilled in the art to which this invention pertains. All publications, patents, and patent applications are herein incorporated by reference to the same extent as if each individual publication or patent application was specifically and individually indicated to be incorporated by reference.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of transforming corn callus tissue or a precultured immature corn embryo comprising the steps of:
    (a) incubating said corn callus tissue or a precultured immature corn embryo in a low-oxygen environment;
    (b) introducing in a low-oxygen environment a nucleic acid sequence into said corn callus tissue or immature corn embryo that was incubated in a low-oxygen environment, resulting in a transformed immature corn embryo or transformed corn callus tissue;
    (c) culturing the transformed immature corn embryo or transformed corn callus tissue on a selective growth medium; and
    (d) regenerating a transformed corn plant from said transformed corn callus tissue or transformed precultured immature corn embryo;
    wherein said low-oxygen environment is between about 2% and about 15% oxygen.

2. The method of claim 1 in which said low-oxygen environment is between about 5% and about 9% oxygen.

3. The method of claim 2 in which said low-oxygen environment is about 7% oxygen.

4. The method of claim 1 in which said nucleic acid sequence is introduced via *Agrobacterium*-mediated transformation.

5. The method of claim 1 in which said nucleic acid sequence is introduced via biolistic transformation.

6. The method of producing a transformed corn plant comprising the steps of:
    (a) incubating corn callus in a low-oxygen environment;
    (b) introducing in a low-oxygen environment a nucleic acid sequence into said corn callus that was incubated in a low-oxygen environment;
    (c) culturing the transformed corn callus on a selective growth medium;
    (d) regenerating a transformed corn plant from said transformed corn callus;
    and wherein said low-oxygen environment is between about 2% and about 15% oxygen.

7. A method of transforming corn callus tissue or a precultured immature corn embryo comprising the steps of:
    (a) incubating said corn callus tissue or a precultured immature corn embryo in a low-oxygen environment;
    (b) introducing in a low-oxygen environment a nucleic acid sequence into said corn callus tissue or immature corn embryo that was incubated in a low-oxygen environment, resulting in a transformed immature corn embryo or transformed corn callus tissue;
    (c) culturing the transformed immature corn embryo or transformed corn callus tissue on a selective growth medium; and
    (d) regenerating a transformed corn plant from said transformed corn callus tissue or transformed precultured immature corn embryo in a low-oxygen environment;
    wherein said low-oxygen environment is between about 2% and about 15% oxygen.

8. A method of producing a transgenic corn plant comprising exposing corn callus tissue or precultured immature corn embryo to a low-oxygen environment before or during introduction of a nucleic acid sequence into the corn callus tissue or precultured immature corn embryo, and then regenerating the transgenic plant from the corn callus tissue or precultured immature corn embryo in a low-oxygen environment, wherein said low-oxygen environment is between about 2% and about 15% oxygen.

9. The method of claim 1, wherein the transformed plant is regenerated in the low oxygen environment.

10. The method of claim 6, wherein the transformed corn plant is regenerated in the low-oxygen environment.

11. The method of claim 6 in which said low-oxygen environment is between about 5% and about 9% oxygen.

12. The method of claim 6 in which said low-oxygen environment is about 7% oxygen.

13. The method of claim 7 in which said low-oxygen environment is between about 5% and about 9% oxygen 14. The method of claim 7 in which said low-oxygen environment is about 7% oxygen.

15. The method of claim 1, wherein the corn callus tissue or a precultured immature corn embryo is maintained in the low-oxygen environment during the step of culturing on the selective growth medium or during the step of regenerating the transformed plant.

16. The method of claim 1, wherein the corn callus tissue or a precultured immature corn embryo is maintained in the low-oxygen environment during the step of culturing on the selective growth medium and during the step of regenerating the transformed plant.

17. The method of claim 6, wherein the corn callus is maintained in the low-oxygen environment during the step of culturing on the selective growth medium or during the step of regenerating the transformed plant.

18. The method of claim 6, wherein the corn callus is maintained in the low-oxygen environment during the step of culturing on the selective growth medium and during the step of regenerating the transformed plant.

19. The method of claim 7, further comprising maintaining the corn immature embryo or corn callus tissue in the low-oxygen environment during step (c).

* * * * *